(12) United States Patent
Ko et al.

(10) Patent No.: US 10,111,915 B1
(45) Date of Patent: Oct. 30, 2018

(54) **METHOD TO TREAT FATTY LIVER DISEASE USING *PARABACTEROIDES GOLDSTEINII***

(71) Applicant: Chang Gung Biotechnology Corp., Taipei (TW)

(72) Inventors: Yun-Fei Ko, Taipei (TW); Jan Martel, Taoyuan (TW); Tsung-Ru Wu, Taoyuan (TW); Chih-Jung Chang, Taoyuan (TW); Chuan-Sheng Lin, Taoyuan (TW); Jian-Ching Liau, Taipei (TW); Wei-Chang Wang, Taipei (TW); Chen-Yaw Chiu, New Taipei (TW); Chia-Chen Lu, New Taipei (TW); David Marcelo Ojcius, Taoyuan (TW); Hsin-Chih Lai, Taoyuan (TW); John D. Young, Taipei (TW)

(73) Assignee: CHANG GUNG BIOTECHNOLOGY CORP., Taipei (TW)

( * ) Notice: Subject to any disclaimer, the term of this patent is extended or adjusted under 35 U.S.C. 154(b) by 0 days.

(21) Appl. No.: 15/815,134

(22) Filed: Nov. 16, 2017

(30) Foreign Application Priority Data

Aug. 28, 2017 (TW) ................. 106129197 A

(51) Int. Cl.
*A61K 49/00* (2006.01)
*A61K 48/00* (2006.01)
*A01N 63/00* (2006.01)
*A61K 35/741* (2015.01)
*A61K 39/00* (2006.01)

(52) U.S. Cl.
CPC ............ *A61K 35/741* (2013.01); *A61K 39/00* (2013.01)

(58) Field of Classification Search
CPC .... A61K 35/00; A61K 35/741; A61K 35/742; A61K 35/744; A61K 39/00; A61K 39/02
USPC ................. 424/9.1, 9.2, 93.1, 93.4
See application file for complete search history.

*Primary Examiner* — Rodney P Swartz
(74) *Attorney, Agent, or Firm* — WPAT, PC

(57) ABSTRACT

The present invention describes a method to reduce blood aspartate transaminase level, liver weight, hepatic lipid accumulation and hepatocyte hypertrophy by administering the probiotic bacterium *Parabacteroides goldsteinii* to a subject showing signs of fatty liver disease. This probiotic bacterium can therefore be used to treat fatty liver disease.

8 Claims, 4 Drawing Sheets

METHOD TO TREAT FATTY LIVER DISEASE USING *PARABACTEROIDES GOLDSTEINII*

CROSS-REFERENCE TO RELATED APPLICATION

This application claims priority of Taiwan patent application No. 106129197, filed on Aug. 28, 2017, the content of which is incorporated herein in its entirety by reference.

BACKGROUND OF THE INVENTION

1. Field of the Invention

The present invention relates to a method for treating fatty liver disease, and more particularly to a method for treating such disease by administering the probiotic bacterium *Parabacteroides goldsteinii*.

2. The Prior Art

Fatty liver disease is a reversible condition in which fat accumulates in the liver (>10%). The condition may lead to liver fibrosis and cirrhosis, dangerous conditions in which the liver no longer functions properly. Fatty liver disease may be caused by various factors, including excessive food or alcohol consumption, metabolic disorders (abetalipoproteinemia, glycogen storage disease, Weber-Christian disease), nutritional deficiencies (malnutrition, severe weight loss, refeeding syndrome, gastric bypass), drugs and toxins (amiodarone, highly active antiretroviral therapy, tamoxifen, methotrexate, glucocorticoids) or others (celiac disease, hepatitis C, inflammatory bowel disease). The incidence of fatty liver disease has considerably increased in recent years, and is found in 10 to 24% of the population, and in as much as 75% of obese people. Fatty liver disease is associated with many preventable causes, indicating that this condition may be prevented by lifestyle changes.

Currently, no pharmaceutical drugs have been specifically approved for the treatment of fatty liver disease. Low-calorie diet, alcohol restriction and regular exercise represent the major strategies used to treat fatty liver disease, but these approaches are difficult to implement and their long-term efficacy has been disappointing. For these reasons, alternative strategies to treat fatty liver disease in a safe and effective manner would be beneficial.

The gut microbiota is involved in various physiological functions, such as energy regulation, toxin neutralization and nutrient absorption. Gut dysbiosis has been noted in patients suffering from fatty liver disease, but it remains unclear whether modulation of the composition of the gut microbiota using prebiotics or probiotics may reduce symptoms and progression of the disease.

SUMMARY OF THE INVENTION

An objective of the present invention is to provide a method for treating fatty liver disease by administering a composition comprising an effective amount of *Parabacteroides goldsteinii* to a subject in need thereof.

According to an embodiment of the present invention, *P. goldsteinii* is a live bacterium.

According to an embodiment of the present invention, the effective amount of *P. goldsteinii* bacterium is between 0.001 CFUs/kg to $5 \times 10^{18}$ CFUs/kg of body weight per day. The effective amount of *P. goldsteinii* bacterium may be approximately $6.1 \times 10^9$ CFUs/individual per day, and the administration period may be around 8 weeks.

According to an embodiment of the present invention, the composition is orally administered to the subject in need thereof. The composition may be orally administered along with food.

According to an embodiment of the present invention, the composition comprises a pharmaceutically acceptable carrier. The composition may be in the form of a solution, gelatin capsule, softgel capsule and pressed tablet. Furthermore, the composition may comprise at least an ingredient selected from the group consisting of proteins, monosaccharides, disaccharides, oligosaccharides, polysaccharides, carbohydrates, amino acids, lipids, vitamins and combinations thereof.

According to an embodiment of the present invention, the composition may comprise other bacteria.

The method disclosed herein can be used to reduce blood aspartate aminotransferase (AST) level, liver weight, hepatic lipid accumulation and hepatocyte hypertrophy in animals and humans, and thus provides a new strategy to treat fatty liver disease.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
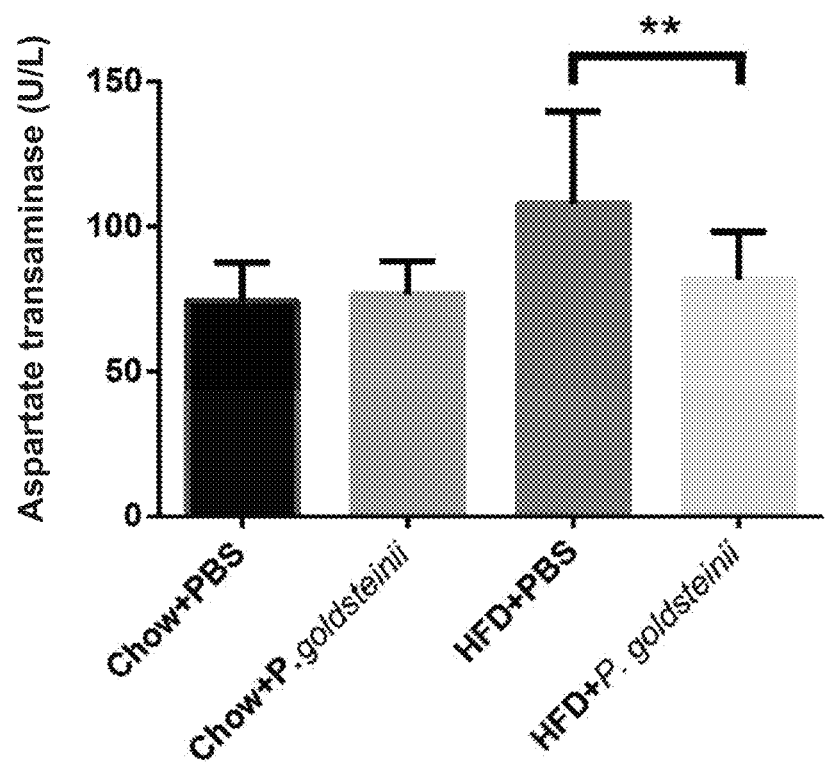
FIG. 1 shows that *P. goldsteinii* supplementation reduces blood aspartate transaminase (AST) level in high-fat diet (HFD)-fed mice.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

The "effective amount" described in the present invention represents the amount of bacteria that can reduce blood AST level, liver weight, hepatic lipid accumulation and hepatocyte hypertrophy in animals and humans. The effective amount may vary depending on the organism or individual treated but can be determined experimentally using various techniques, including a dose escalation study.

As used herein, the data provided represent experimental values that can vary within a range of ±20%, preferably within ±10%, and most preferably within ±5%.

*Parabacteroides goldsteinii*

The bacterium strain *P goldsteinii* (ATCC BAA-1180) used in the following examples was purchased from the American Type Culture Collection (ATCC, USA) and cultured in liquid thioglycollate medium under anaerobic conditions (DG250 Anaerobic Workstation, Don Whitley Scientific, UK) containing 10% carbon dioxide, 10% hydrogen and 80% nitrogen at 37° C.

The present invention provides a method to treat fatty liver disease comprising: administering an effective amount of *P goldsteinii* bacteria to an individual who shows signs of fatty liver disease. The examples below show the effects of *P goldsteinii* bacteria on blood AST level, liver weight, hepatic lipid accumulation and hepatocyte size. Generally, *P goldsteinii* bacteria can be given to mammals and humans at a dose ranging from 0.001 CFUs/kg to $5 \times 10^{18}$ CFUs/kg per day. The invention is described in detail below.

Example 1

Effects of *P goldsteinii* Bacterium Treatment on Blood AST Level in HFD-Fed Mice Eight-week old C57BL/6J male mice were fed with standard chow (13.5% of energy from fat; LabDiet 5001; LabDiet, USA) in the control group or with HFD (60% of energy from fat; TestDiet 58Y1; TestDiet, USA) in the experimental group. The mice were also treated daily with 200 μl of *P. goldsteinii* ATCC strain BAA-1180 ($2 \times 10^6$ CFUs) or PBS for 8 weeks by intragastric gavage (n=10 mice/group). The mice were assigned to four groups: (1) mice fed with standard chow and treated with phosphate buffered saline (Chow+PBS); (2) mice fed with standard chow and treated with *P. goldsteinii* (Chow+*P. goldsteinii*); (3) mice fed with HFD and treated with PBS (HFD+PBS); and (4) mice fed with HFD and treated with *P. goldsteinii* (HFD+*P. goldsteinii*).

After 8 weeks, blood samples were collected from each mouse, and AST level was quantified using a biochemical analyzer (Hitachi 7080, Hitachi, Japan). Data were presented as means±standard deviation (n=10 mice/group), and analyzed using one-way ANOVA followed by Bonferroni post hoc test (**$P<0.01$).

FIG. 1 shows the effects of *P. goldsteinii* according to the present invention on blood. AST concentration in chow-fed and HFD-fed mice. As seen in the figure, feeding with the HFD (HFD+PBS) increased AST concentration compared to feeding with chow (Chow+PBS). Notably, mice treated with HFD+*P. goldsteinii* showed a reduce AST level compared to HFD-fed mice (HFD+PBS), indicating that the *P. goldsteinii* treatment according to the present invention has the effect of reducing blood AST level in a subject in need thereof.

Example 2

Effects of *P. goldsteinii* Bacterium Treatment on Liver Weight in HFD-Fed Mice

Eight-week old C57BL/6J male mice were treated as in Example 1 and assigned to four groups consisting of Chow+PBS, Chow+*P. goldsteinii*, HFD+PBS and HFD+*P. goldsteinii*. After 8 weeks, liver tissues from each mouse were dissected and weighted. Data were presented as means±standard deviation (n=10 mice/group) and analyzed using one-way ANOVA followed by Bonferroni post hoc test (**$P<0.01$).

Figure 2:
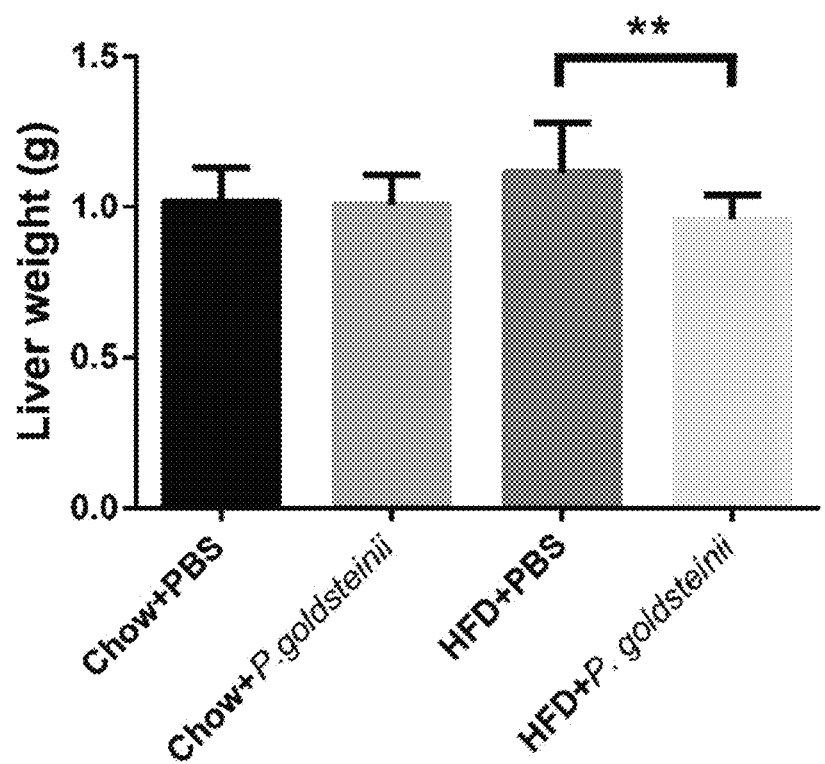
FIG. 2 shows that *P. goldsteinii* supplementation reduces liver weight in HFD-fed mice.

FIG. 2 shows the effects of *P. goldsteinii* on liver weight. HFD feeding (HFD+PBS) for 8 weeks increased liver weight compared to feeding with chow (Chow+PBS). By contrast, supplementation with *P. goldsteinii* (HFD+*P. goldsteinii*) reduced liver weight in a statistically significant manner compared to the HFD group (HFD+PBS) indicating that the *P. goldsteinii* treatment described in the present n has the effect of reducing liver weight in a subject in need thereof.

Example 3

Effects of *P. goldsteinii* Bacterium Treatment on Lipid Accumulation in the Liver of HFD-Fed Mice Eight-week old C57BL/6J male mice were treated as in Example 1 and assigned to four groups (Chow+PBS, Chow+*P. goldsteinii*, HFD+PBS and HFD+*P. goldsteinii*). After 8 weeks, liver tissues from each mouse were dissected and frozen to prepare tissue sections. Frozen liver sections (6-μm thick) were stained with oil red O (Sigma, USA), and counter-stained with haematoxylin for 1 min. Sections were then examined under light microscopy (scale bar, 100 μm).

Figure 3:
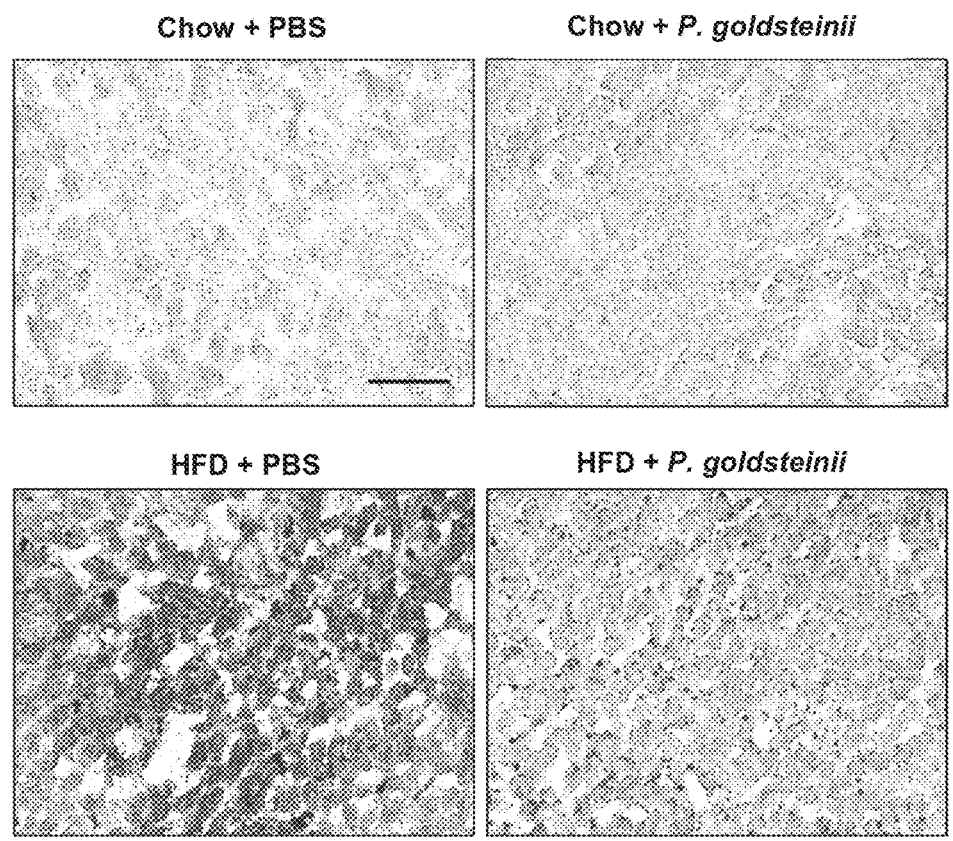
FIG. 3 shows that *P. goldsteinii* supplementation reduces lipid accumulation in the liver of HFD-fed mice.

FIG. 3 shows the effects of *P. goldsteinii* supplementation on lipid accumulation in the liver. While HFD feeding (HFD+PBS) increased lipid accumulation in the liver compared to feeding with chow (Chow+PBS), the *P. goldsteinii* treatment (HFD+*P. goldsteinii*) reduced hepatic lipid accumulation compared to the HFD group (HFD+PBS), indicating that the *P. goldsteinii* treatment disclosed in the present invention reduces lipid accumulation in the liver of a subject in need thereof.

Example 4

Effects of *P. goldsteinii* Bacterium Treatment on Hepatocyte Hypertrophy in HFD-Fed Mice Eight-week old C57BL/6J male mice were treated as in Example 1. After 8 weeks, liver tissues of each individual were removed and stained with hematoxilin and eosin (H&E), and then observed under light microscopy (n=4 to 5 images/mouse; n=10 mice/group; scale bar, 100 μm).

Figure 4:
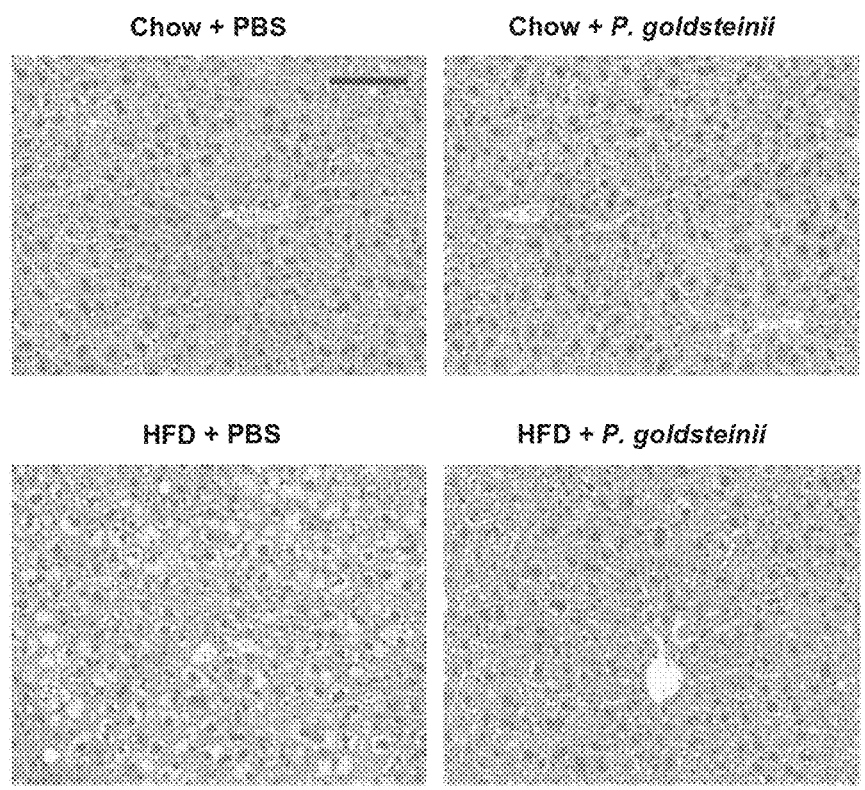
FIG. 4 shows that *P. goldsteinii* supplementation reduces hepatocyte hypertrophy in HFD-fed mice.

FIG. 4 shows the effects of *P. goldsteinii* on hepatocyte hypertrophy. Feeding mice with a HFD (HFD+PBS) for 8 weeks increased hepatocyte size compared to the chow diet (Chow+PBS). However, Supplementation with *P. goldsteinii* (HFD+*P. goldsteinii*) for this period considerably reduced hepatocyte size compared to the HFD group (HFD+PBS) indicating that *P. goldsteinii* reduces hepatocyte size in a subject in need thereof.

As seen in FIGS. 1-4, the composition comprising *P. goldsteinii* according to the present invention can reduce signs of fatty liver disease HFD-fed mice. Based on these results, the effective amount of *P. goldsteinii* required to produce protective effects on fatty liver disease in mice (with an average body weight of 23 g) is about $8.7 \times 10^7$ CFUs/kg per day (for a period of 8 weeks). Accordingly, the effective amount of *P. goldsteinii* that would produce similar effects in a human subject (with an average weight of 70 kg) is estimated at $6.1 \times 10^9$ CFUs/individual (for a period of 8 weeks).

Example 5

Effects of P. goldsteinii Bacterium Treatment on Blood Biochemical Parameters in Chow-Fed Mice The effects of P. goldsteinii treatment on blood biochemical parameters in chow-fed mice were evaluated. The parameters examined include hepatic functions (i.e., levels of aspartate transaminase, AST, and alanine transaminase, ALT) and renal functions (i.e., levels of blood urea nitrogen, BUN, and creatinine). These blood biochemical parameters were monitored using a biochemical analyzer (Hitachi 7080, Hitachi, Japan). As shown in TABLE 1, no statistical differences were noted between the blood biochemical parameters of the Chow+PBS group and those of the Chow+P. goldsteinii group, indicating that administration of P. goldsteinii did not affect liver or kidney functions under these conditions.

TABLE 1

Analysis of liver and kidney functions in mice treated with P. goldsteinii

|  | Chow + PBS | Chow + P. goldsteinii |
| --- | --- | --- |
| Aspartate transaminase (AST; U/l) | 73.9 ± 13.4 | 72.4 ± 19.9 |
| Alanine transaminase (ALT; U/l) | 30.4 ± 11.2 | 26.3 ± 4.8 |
| Blood urea nitrogen (BUN; mg/dl) | 29.8 ± 3.8 | 28.3 ± 2.8 |
| Creatinine (mg/dl) | 0.20 ± 0.05 | 0.20 ± 0.04 |

The data presented are based on triplicate experiments (n = 14-16 mice per group in total).

As described above, the composition comprising P. goldsteinii bacteria according to one embodiment of the present invention can be administrated orally. The composition can be added to the diet of a subject, as a drug, a drink, a daily supplement, or a food, without incurring in significant lifestyle changes, toxicity or other unfavorable health conditions.

Moreover, the composition comprising P. goldsteinii bacteria according to one embodiment of the present invention may further comprise a pharmaceutically acceptable carrier known to a person skilled in the art. The composition may be in the form of a solution, gelatin capsule, softgel capsule, pressed tablet and the like. Furthermore, the composition may comprise at least an inert or active ingredient selected from the group consisting of proteins, monosaccharides, disaccharides, oligosaccharides, polysaccharides, carbohydrates, amino acids, lipids, vitamins and combinations thereof.

The present invention provides a method for treating fatty liver disease using the probiotic bacterium P. goldsteinii. This bacterium can be used to reduce blood AST level, liver weight, hepatic lipid accumulation and hepatocyte hypertrophy in animals and humans. Thus, the present invention provides a new strategy to protect against fatty liver disease in humans, and has obvious commercial applications in view of the large number of products and treatments available on the market to treat fatty liver disease.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating fatty liver disease in a subject on a high fat diet, comprising administering a composition comprising an effective amount of *Parabacteroides goldsteinii* bacterium, wherein the composition is orally administered to the subject for at least eight weeks.

2. The method according to claim 1, wherein the *Parabacteroides goldsteinii* bacterium is a live bacterium.

3. The method according to claim 1, wherein the effective amount of the *Parabacteroides goldsteinii* bacterium is between 0.001 CFUs/kg to $5\times10^{18}$ CFUs/kg of body weight per day.

4. The method according to claim 1, wherein the effective amount of the *Parabacteroides goldsteinii* bacterium is $6.1\times10^9$ CFUs/individual per day.

5. The method according to claim 1, wherein the composition further comprises a pharmaceutically acceptable carrier.

6. The method according to claim 5, wherein the composition is in the form of a solution, gelatin capsule, softgel capsule or pressed tablet.

7. The method according to claim 1, wherein the composition further comprises at least an ingredient selected from the group consisting of proteins, mono saccharides, disaccharides, oligo saccharides, polysaccharides, carbohydrates, amino acids, lipids, vitamins and combinations thereof.

8. The method according to claim 1, wherein the composition further comprises other bacteria.

\* \* \* \* \*